US009781953B2

(12) United States Patent
Verleur et al.

(10) Patent No.: US 9,781,953 B2
(45) Date of Patent: Oct. 10, 2017

(54) VAPORIZER WITH COVER SLEEVE

(71) Applicant: VMR Products, LLC, Miami, FL (US)

(72) Inventors: Jan Andries Verleur, Miami Beach, FL (US); Dan Recio, Miami, FL (US)

(73) Assignee: VMR Products LLC, Miami, FL (US)

( * ) Notice: Subject to any disclaimer, the term of this patent is extended or adjusted under 35 U.S.C. 154(b) by 254 days.

(21) Appl. No.: 14/543,389

(22) Filed: Nov. 17, 2014

(65) Prior Publication Data

US 2015/0136155 A1    May 21, 2015

Related U.S. Application Data

(60) Provisional application No. 61/905,093, filed on Nov. 15, 2013.

(51) Int. Cl.
*A24F 47/00* (2006.01)
*H05B 1/02* (2006.01)

(52) U.S. Cl.
CPC ......... *A24F 47/008* (2013.01); *H05B 1/0208* (2013.01); *H05B 1/0244* (2013.01)

(58) Field of Classification Search
CPC .... A24F 47/008; A61M 15/06; H05B 1/0244; H05B 1/0208
USPC ....................................................... 131/328
See application file for complete search history.

(56) References Cited

U.S. PATENT DOCUMENTS

| | | |
|---|---|---|
| 1,446,087 A | 2/1923 | Griffin |
| 2,057,353 A | 10/1936 | Whittemore, Jr. |
| 2,545,851 A | 3/1951 | Kardos |
| 3,060,429 A | 10/1962 | Winston |
| 3,200,819 A | 8/1965 | Gilbert |
| 3,203,025 A | 8/1965 | Schreur |
| 3,400,998 A | 9/1968 | Daugherty et al. |
| 3,479,561 A | 11/1969 | Janning |
| 3,502,588 A | 3/1970 | Winberg |
| 3,747,120 A | 7/1973 | Stemme |
| D248,047 S | 5/1978 | Rappoport |
| D251,072 S | 2/1979 | Stuetzer |
| 4,207,457 A | 6/1980 | Haglund et al. |
| D257,519 S | 11/1980 | Plozner |
| D259,588 S | 6/1981 | Stutzer |

(Continued)

FOREIGN PATENT DOCUMENTS

| | | |
|---|---|---|
| CA | 2 846 286 A1 | 4/2013 |
| CN | 1233436 A | 11/1999 |

(Continued)

OTHER PUBLICATIONS

European Patent Office Search Report mailed Oct. 12, 2015 for EP Application No. 14159710.4, filed Mar. 14, 2014.

(Continued)

*Primary Examiner* — Joseph S Del Sole
*Assistant Examiner* — Mohamed K Ahmed Ali
(74) *Attorney, Agent, or Firm* — Brinks Gilson & Lione

(57) ABSTRACT

A vaporizer may include a battery portion, a cartomizer connectable with the battery portion, and a sleeve fitable over the cartomizer. The sleeve and an outer shell of the battery portion may have the same or complimentary colors or patterns. The battery portion may further include a plurality of illuminable indicators, which may illuminate to indicate, for instance, remaining voltage of a battery housed within the battery portion.

10 Claims, 1 Drawing Sheet

(56) References Cited

U.S. PATENT DOCUMENTS

| | | |
|---|---|---|
| D260,690 S | 9/1981 | Stutzer |
| D260,941 S | 9/1981 | Figur |
| 4,569,136 A | 2/1986 | Loring |
| 4,676,237 A | 6/1987 | Wood et al. |
| 4,771,295 A | 9/1988 | Baker et al. |
| 4,771,796 A | 9/1988 | Myer |
| 4,797,692 A | 1/1989 | Ims |
| 4,848,374 A | 7/1989 | Chard et al. |
| 4,945,448 A | 7/1990 | Bremenour et al. |
| 4,945,929 A | 8/1990 | Egilmex |
| 4,972,855 A | 11/1990 | Kuriyama et al. |
| 4,990,939 A | 2/1991 | Sekiya et al. |
| 5,060,671 A | 10/1991 | Counts et al. |
| 5,124,200 A | 6/1992 | Mallonee |
| 5,144,962 A | 9/1992 | Counts et al. |
| 5,224,265 A | 7/1993 | Dux et al. |
| 5,327,915 A | 7/1994 | Porenski et al. |
| 5,388,574 A | 2/1995 | Ingebrethsen |
| 5,505,214 A | 4/1996 | Collins et al. |
| 5,646,666 A | 7/1997 | Cowger et al. |
| 5,666,977 A | 9/1997 | Higgins et al. |
| 5,703,633 A | 12/1997 | Gehrer et al. |
| 5,743,251 A | 4/1998 | Howell et al. |
| 5,819,756 A | 10/1998 | Mielordt |
| 5,894,841 A | 4/1999 | Voges |
| 5,996,589 A | 12/1999 | St. Charles |
| 6,062,213 A | 5/2000 | Fuisz et al. |
| 6,155,268 A | 12/2000 | Takeuchi |
| 6,196,218 B1 | 3/2001 | Voges |
| 6,234,167 B1 | 5/2001 | Cox et al. |
| 6,322,268 B1 | 11/2001 | Kaufmann et al. |
| 6,471,782 B1 | 10/2002 | Fang et al. |
| 6,501,052 B2 | 12/2002 | Cox et al. |
| 6,598,607 B2 | 7/2003 | Adiga et al. |
| 6,620,659 B2 | 9/2003 | Emmma et al. |
| 6,701,921 B2 | 3/2004 | Sprinkel, Jr. et al. |
| 6,719,443 B2 | 4/2004 | Gutstein et al. |
| 6,722,763 B1 | 4/2004 | Hsu et al. |
| 7,059,307 B2 | 6/2006 | Pellizzari et al. |
| D531,180 S | 10/2006 | Goto |
| 7,143,766 B2 | 12/2006 | Schuster et al. |
| D624,238 S | 9/2010 | Turner |
| D642,330 S | 7/2011 | Turner |
| D644,375 S | 8/2011 | Zhou |
| D645,816 S | 9/2011 | Sasada et al. |
| D675,777 S | 2/2013 | Wu |
| 8,365,742 B2 | 2/2013 | Hon |
| 8,375,957 B2 | 2/2013 | Hon |
| 8,393,331 B2 | 3/2013 | Hon |
| 8,490,628 B2 | 7/2013 | Hon |
| D688,415 S | 8/2013 | Kim |
| D693,053 S | 11/2013 | Chen |
| D693,765 S | 11/2013 | Workman et al. |
| D695,450 S | 12/2013 | Benassayag et al. |
| D702,876 S | 4/2014 | Liu |
| D704,634 S | 5/2014 | Eidelman et al. |
| D718,492 S | 11/2014 | Albanese |
| D720,094 S | 12/2014 | Alima |
| D720,095 S | 12/2014 | Alima |
| D720,496 S | 12/2014 | Alima |
| D720,497 S | 12/2014 | Alima |
| D720,881 S | 1/2015 | Liu |
| D720,882 S | 1/2015 | Albanese |
| D720,883 S | 1/2015 | Albanese |
| D721,202 S | 1/2015 | Liu |
| D722,166 S | 2/2015 | Buehl et al. |
| D722,956 S | 2/2015 | Alima |
| 8,955,522 B1 | 2/2015 | Bowen et al. |
| D724,263 S | 3/2015 | Malhi |
| D724,782 S | 3/2015 | Wu |
| D725,310 S | 3/2015 | Eksouzian |
| D726,364 S | 4/2015 | Weigensberg |
| D729,441 S | 5/2015 | Hua |
| 9,038,642 B2 | 5/2015 | Liu |
| D732,733 S | 6/2015 | Spagnolo et al. |
| 2005/0017685 A1 | 1/2005 | Rees et al. |
| 2006/0093977 A1 | 5/2006 | Pellizzari et al. |
| 2008/0257367 A1 | 10/2008 | Paterno et al. |
| 2011/0220234 A1 | 9/2011 | Haas |
| 2011/0277761 A1 | 11/2011 | Terry et al. |
| 2012/0318882 A1 | 12/2012 | Abehasera |
| 2013/0042865 A1 | 2/2013 | Monsees et al. |
| 2013/0152922 A1 | 6/2013 | Benassayag et al. |
| 2013/0180533 A1 | 7/2013 | Kim et al. |
| 2013/0192615 A1* | 8/2013 | Tucker .............. H01C 17/00 131/328 |
| 2013/0192617 A1 | 8/2013 | Thompson |
| 2013/0199528 A1 | 8/2013 | Goodman et al. |
| 2013/0213420 A1 | 8/2013 | Hon |
| 2013/0220315 A1 | 8/2013 | Conley et al. |
| 2013/0284190 A1 | 10/2013 | Scatterday et al. |
| 2013/0284194 A1 | 10/2013 | Newton |
| 2013/0298905 A1 | 11/2013 | Levin et al. |
| 2014/0034070 A1 | 2/2014 | Schennum |
| 2014/0041655 A1 | 2/2014 | Barron et al. |
| 2014/0261499 A1 | 9/2014 | Hon |
| 2015/0027467 A1 | 1/2015 | Liu |
| 2015/0027471 A1 | 1/2015 | Feldman et al. |
| 2015/0091501 A1 | 4/2015 | Claudepierre |

FOREIGN PATENT DOCUMENTS

| | | |
|---|---|---|
| CN | 201018927 Y | 2/2008 |
| CN | 203087525 U | 7/2013 |
| CN | 203182012 U | 9/2013 |
| EP | 0 358 114 A2 | 3/1990 |
| EP | 0 533 599 A1 | 3/1993 |
| EP | 0 845 220 A1 | 6/1998 |
| EP | 2 654 471 B1 | 10/2013 |
| KR | 101 011 453 B1 | 1/2011 |
| WO | 98/17131 A1 | 4/1998 |
| WO | 02/098390 A2 | 12/2002 |
| WO | 03/000324 A1 | 1/2003 |
| WO | 03/034847 A1 | 5/2003 |
| WO | 2007/078273 A1 | 7/2007 |
| WO | 2012/072762 A1 | 6/2012 |
| WO | 2013/034453 A1 | 3/2013 |
| WO | 2013/093695 A1 | 6/2013 |
| WO | 2013/116567 A1 | 8/2013 |
| WO | 2013/155645 A1 | 10/2013 |
| WO | 2013/159245 A1 | 10/2013 |
| WO | 2014/008646 A1 | 1/2014 |

OTHER PUBLICATIONS

European Patent Office, Partial European Search Report mailed Oct. 13, 2015 for EP Application No. 14159709.6 filed Mar. 14, 2014.
International Search Report for PCT/US2014/065971, filed Nov. 17, 2014, search mailed on Feb. 11, 2015, 2pp.
Written Opinion of the ISA for PCT/US2014/065971, filed Nov. 17, 2014, opinion mailed on Feb. 11, 2015, 9pp.
Andrus et al., "Nicotine microaerosol inhaler", Canadian Respiratory Journal, Nov./Dec. 1999, pp. 509-512, Vo. 6, No. 6.
"What is a MOSFET, what does it look like, and how does it work?" dated May 24, 2004, printed from the Internet Archive, i.e., the Wayback machine, which was archived on Mar. 5, 2010 ("TechPowerUp").
"What is a MOSFET, what does it look like, and how does it work?" dated May 24, 2004, printed from the Internet Archive, i.e., the Wayback machine, which was archived on Jul. 20, 2011 ("TechPowerUp").
Extended European Search Report issued in counterpart European Pat. Appln. No. EP 14861400.1 dated Jun. 8, 2017.

* cited by examiner

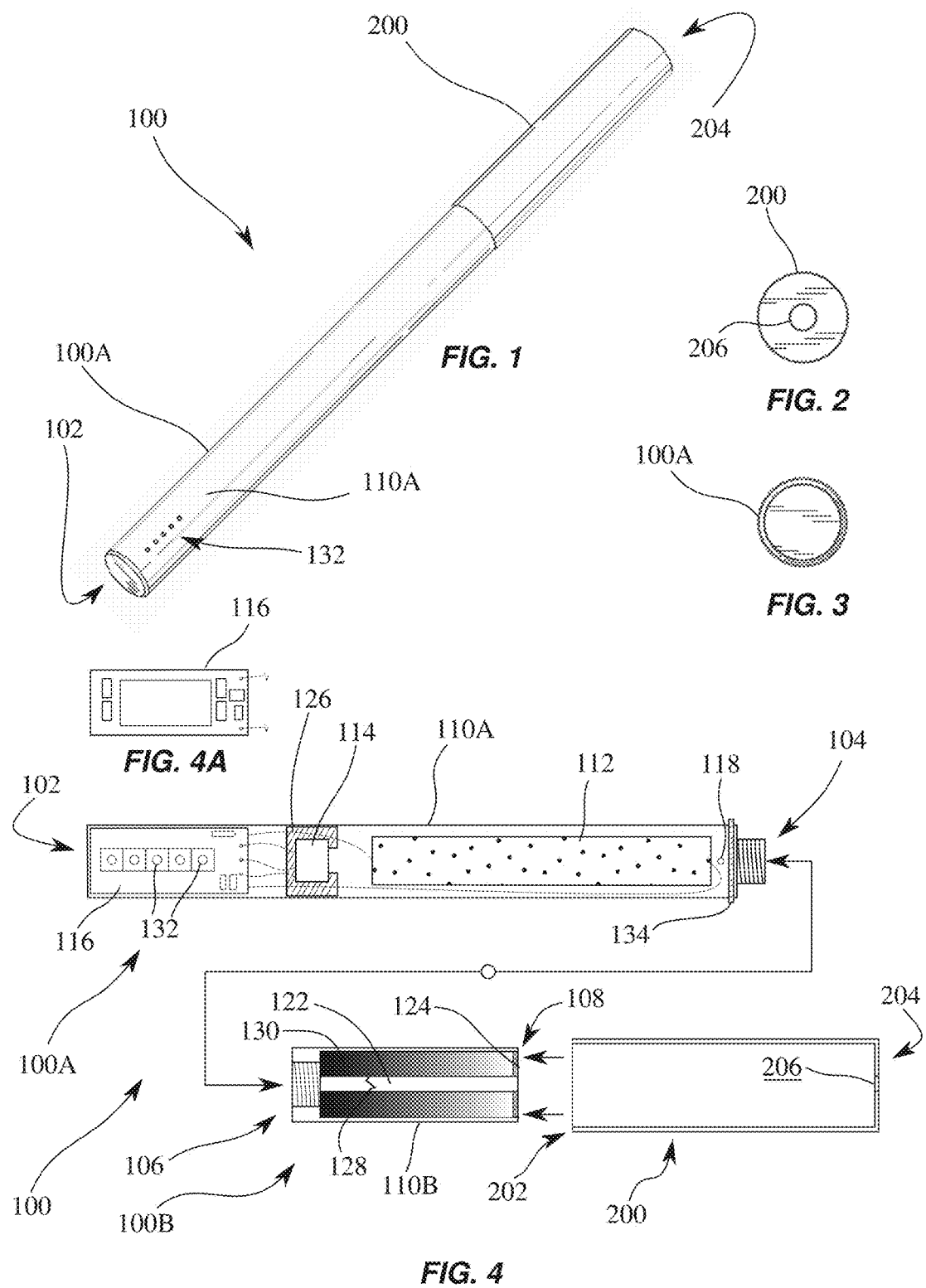

VAPORIZER WITH COVER SLEEVE

CROSS REFERENCE TO RELATED APPLICATIONS

This application claims the benefit of U.S. Provisional Application No. 61/905,093 filed Nov. 15, 2013, the disclosure of which is hereby incorporated herein by reference in its entirety.

FIELD OF THE DISCLOSURE

This disclosure relates generally to the field of vaporizers, which may also be referred to as electronic cigarettes.

BACKGROUND

Electronic cigarettes have recently emerged as a new product for providing nicotine through a smokeless inhalation process. Typically, implementations consist of a power supply (typically a battery) and an atomizing device. In reusable electronic cigarettes the two items are separated into a battery and a cartomizer, to allow the disposal and replacement of a nicotine containing fluid cartomizer while preserving the more costly battery and associated circuitry (microcontroller, switch, etc.) for additional use. In disposable electronic cigarettes, the two items are combined to integrate the functions into one unit that is discarded after either the battery energy or the nicotine containing liquid is exhausted.

The electronic cigarette liquid used to vaporize ingredients such as nicotine is generally a solution of propylene glycol (PG), vegetable glycerin (VG), or polyethylene glycol 400 (PEG400), as well as their mixtures to which a flavor and/or nicotine has been added. The solution is often sold in a bottle (for refilling by the user) or in disposable cartridges or cartomizers. Many different flavors are incorporated into these liquids, including those that resemble the taste of regular tobacco, menthol, vanilla, coffee, cola and/or various fruits. Various nicotine concentrations are also available, and nicotine-free solutions are also common.

BRIEF SUMMARY OF THE DISCLOSURE

The following presents a simplified summary of the disclosure in order to provide a basic understanding of some aspects of the invention. This summary is not an extensive overview of the invention. It is intended to neither identify key or critical elements of the invention nor delineate the scope of the invention. Its sole purpose is to present some concepts of the invention, in accordance with the disclosure, in a simplified form as a prelude to the more detailed description that is presented later.

In one embodiment of the disclosure, a vaporizer may include a battery portion including an outer shell having an outer shell diameter, a plurality of holes thereby permitting airflow to be established through at least a section of the battery portion, and internal components housed within the outer shell. The internal components may include a battery, a printed circuit board, including a microcontroller for operating a program to control the vaporizer, a pressure switch operable to detect a pressure differential generated when the airflow is established, at least one illuminable indicator which illuminates in association with charge remaining of the battery, and electronic circuitry housed within the outer shell, the electronic circuitry electrically connecting the battery, the printed circuit board, the pressure switch, and the at least one illuminable indicator. The vaporizer may further include a cartomizer including a cartomizer outer shell having a cartomizer outer shell diameter substantially similar to the outer shell diameter, the cartomizer connectable with the battery portion, the cartomizer including internal cartomizer components housed within the outer cartomizer shell. The internal cartomizer components may include a heating element electrically connected with the electronic circuitry of the battery portion when the cartomizer and the battery portion are connected, the heating element operable to heat to a vaporization temperature when a current is passed along the heating element, a storage component for holding a vaporizable fluid, and a tube in fluid communication between the airflow of the battery portion and a mouthpiece provided on the cartomizer outer shell.

An additional embodiment of a vaporizer may include a battery portion including an outer shell having an outer shell diameter, a plurality of holes thereby permitting airflow to be established through at least a section of the battery portion, a retaining ring provided externally on an area of the outer shell, and internal components housed within the outer shell. The internal components may include a battery, a printed circuit board, including a microcontroller for operating a program to control the vaporizer, a pressure switch operable to detect a pressure differential generated when the airflow is established, a plurality of light emitting diodes which illuminate in association with charge remaining of the battery, and electronic circuitry housed within the outer shell, the electronic circuitry electrically connecting the battery, the printed circuit board, the pressure switch, and the at least one illuminable indicator. The vaporizer may further include a cartomizer including a cartomizer outer shell having a cartomizer outer shell diameter substantially similar to the outer shell diameter, the cartomizer connectable with the battery portion, the cartomizer including internal cartomizer components housed within the outer cartomizer shell. The internal cartomizer components may include a heating element electrically connected with the electronic circuitry of the battery portion when the cartomizer and the battery portion are connected, the heating element operable to heat to a vaporization temperature when a current is passed along the heating element, a storage component for holding a vaporizable fluid, and a tube in fluid communication between the airflow of the battery portion and a mouthpiece provided on the cartomizer outer shell. The vaporizer may also include a sleeve having dimensions conforming with the cartomizer, the sleeve fitable over the cartomizer, the sleeve including an air hole alignable with the mouthpiece of the cartomizer when the sleeve is fitted the cartomizer, the retaining ring contacting an internal surface of the vaporizer sleeve when the vaporizer sleeve is placed over the cartomizer and the cartomizer is connected with battery portion.

BRIEF DESCRIPTION OF THE FIGURES

The following description and the annexed drawings set forth certain illustrative aspects of the invention. These aspects are indicative, however, of but a few of the various ways in which the principles of the invention may be employed and the present invention is intended to include all such aspects and their equivalents. Other advantages and novel features of the invention will become apparent from the following description when considered in conjunction with the drawings.

FIG. 1 illustrates a perspective view of an embodiment of a vaporizer with a vaporizer sleeve in accordance with the disclosure;

FIG. 2 illustrates a front view of the vaporizer with the vaporizer sleeve of FIG. 1;

FIG. 3 illustrates a rear view of the vaporizer with the vaporizer sleeve of FIG. 1;

FIG. 4 illustrates an exploded side view of a vaporizer, without a vaporizer sleeve, in accordance with the disclosure, with the outer shell of the vaporizer transparent thereby illustrating the internal components of the vaporizer; and FIG. 4A illustrates a reverse side view of the printed circuit board of the vaporizer shown in FIG. 4.

DETAILED DESCRIPTION

The following detailed description and the appended drawings describe and illustrate some embodiments of the invention for the purpose of enabling one of ordinary skill in the relevant art to make and use the invention. As such, the detailed description and illustration of these embodiments are purely illustrative in nature and are in no way intended to limit the scope of the invention, or its protection, in any manner. It should also be understood that the drawings are not to scale and in certain instances details have been omitted, which are not necessary for an understanding of the present invention, such as details of fabrication and assembly. In the accompanying drawings, like numerals represent like components.

In one embodiment of the disclosure, a vaporizer may include a battery portion including an outer shell having an outer shell diameter, a plurality of holes thereby permitting airflow to be established through at least a section of the battery portion, and internal components housed within the outer shell. The internal components may include a battery, a printed circuit board, including a microcontroller for operating a program to control the vaporizer, a pressure switch operable to detect a pressure differential generated when the airflow is established, at least one illuminable indicator which illuminates in association with charge remaining of the battery, and electronic circuitry housed within the outer shell, the electronic circuitry electrically connecting the battery, the printed circuit board, the pressure switch, and the at least one illuminable indicator. The vaporizer may further include a cartomizer including a cartomizer outer shell having a cartomizer outer shell diameter substantially similar to the outer shell diameter, the cartomizer connectable with the battery portion, the cartomizer including internal cartomizer components housed within the outer cartomizer shell. The internal cartomizer components may include a heating element electrically connected with the electronic circuitry of the battery portion when the cartomizer and the battery portion are connected, the heating element operable to heat to a vaporization temperature when a current is passed along the heating element, a storage component for holding a vaporizable fluid, and a tube in fluid communication between the airflow of the battery portion and a mouthpiece provided on the cartomizer outer shell.

Embodiments of a vaporizer may further include at least one illuminable indicator comprises a plurality of light emitting diodes, and wherein the PCB operates to illuminate a predetermined number of light emitting diodes after determining the battery voltage. The plurality of light emitting diodes may include five light emitting diodes, and all five diodes may illuminate if the battery has at least first predetermined level of volts, four diodes may illuminate if the battery has at least a second predetermined level of volts, three diodes may illuminate if the battery has at least a third predetermined level of volts, two diodes may illuminate if a the battery has at least a fourth predetermined level of volts, one diode may illuminate if the battery has at least a fifth predetermined level of volts, and no diode may illuminate if the battery has less than the fifth predetermined level of volts. The vaporize may include a sleeve having dimensions conforming with the cartomizer, the sleeve fitable over the cartomizer. The sleeve may include an air hole alignable with the mouthpiece of the cartomizer when the sleeve is fitted the cartomizer. An outer surface of the sleeve may include a pattern or color which is the same or complimentary as a pattern or color provided on an outer surface of battery portion. The battery portion further include a retaining ring provided on external area of the outer shell of the battery portion, the retaining ring may contact an internal surface of the vaporizer sleeve when the vaporizer sleeve is placed over the cartomizer and the cartomizer is connected with battery portion. The retaining ring may be provided in a recess of the outer shell of the battery portion. The pressure switch may be encapsulated in an elastic material in order to prevent air flow around the pressure switch.

An additional embodiment of a vaporizer may include a battery portion including an outer shell having an outer shell diameter, a plurality of holes thereby permitting airflow to be established through at least a section of the battery portion, a retaining ring provided externally on an area of the outer shell, and internal components housed within the outer shell. The internal components may include a battery, a printed circuit board, including a microcontroller for operating a program to control the vaporizer, a pressure switch operable to detect a pressure differential generated when the airflow is established, a plurality of light emitting diodes which illuminate in association with charge remaining of the battery, and electronic circuitry housed within the outer shell, the electronic circuitry electrically connecting the battery, the printed circuit board, the pressure switch, and the at least one illuminable indicator. The vaporizer may further include a cartomizer including a cartomizer outer shell having a cartomizer outer shell diameter substantially similar to the outer shell diameter, the cartomizer connectable with the battery portion, the cartomizer including internal cartomizer components housed within the outer cartomizer shell. The internal cartomizer components may include a heating element electrically connected with the electronic circuitry of the battery portion when the cartomizer and the battery portion are connected, the heating element operable to heat to a vaporization temperature when a current is passed along the heating element, a storage component for holding a vaporizable fluid, and a tube in fluid communication between the airflow of the battery portion and a mouthpiece provided on the cartomizer outer shell. The vaporizer may also include a sleeve having dimensions conforming with the cartomizer, the sleeve fitable over the cartomizer, the sleeve including an air hole alignable with the mouthpiece of the cartomizer when the sleeve is fitted the cartomizer, the retaining ring contacting an internal surface of the vaporizer sleeve when the vaporizer sleeve is placed over the cartomizer and the cartomizer is connected with battery portion.

In further embodiments of the vaporizer, the retaining ring may be provided in a recess of the outer shell of the battery portion. The pressure switch may be encapsulated in an elastic material in order to prevent air flow around the pressure switch. The plurality of light emitting diodes may include five light emitting diodes, and all five diodes may illuminate if the battery has at least first predetermined level of volts, four diodes may illuminate if the battery has at least a second predetermined level of volts, three diodes may illuminate if the battery has at least a third predetermined level of volts, two diodes may illuminate if a the battery has at least a fourth predetermined level of volts, one diode may illuminate if the battery has at least a fifth predetermined level of volts, and no diode may illuminate if the battery has less than the fifth predetermined level of volts.

With reference now to the figures, an embodiment of a vaporizer 100 with a removable vaporizer sleeve 200 are illustrated. Vaporizer 100 may include a battery portion 100A and a cartomizer 100B. In some embodiments, cartomizer 100B may share a common housing with battery portion 100A, however the illustrated embodiment shows battery portion 100A as removably connectable with cartomizer 100B.

Battery portion may have a first distal end 102 and a second proximate end 104. Cartomizer may have a first battery-side end 106 and a second mouthpiece-side end 108, and battery portion 100A and cartomizer 100B may be connectable at proximate end 104 and battery-side end 106. Battery portion 100A and cartomizer 100B may be connectable by an known or to be developed connectors, including as illustrated matable male and female threading. Battery portion 100A may include an outer battery shell 110A having a diameter similar, or nearly identical, as the diameter of an outer cartomizer shell 110B. Accordingly, when battery portion 100A and cartomizer 100B are mated, vaporizer 100 may be substantially elongate and cylindrical. In some embodiments, the diameter of vaporizer 100 is approximately 9 mm.

Battery portion 100A may include a variety of components housed within outer shell 110A. One such component may be a rechargeable battery 112, which in one embodiment is a lithium-ion battery. A pressure switch 114 and a printed circuit board (PCB) 116 may also be housed within outer shell 110A. Electronic circuity may be further provided in order to electrically connect battery 112, pressure switch 114, and PCB 116 as part of the operation of vaporizer 100. At least one air hole 118 may be provided on outer shell 110, proximate to either end of battery portion 100A, with at least one additional air hole (not illustrated) provided on or proximate to proximate end 104 in order to establish internal air flow through battery portion 100A. The at least one additional air hole may be in fluid communication with at least one battery-side air hole (not illustrated) provided on cartomizer 100B, which in turn may be fluidly communicable with a tube 122 passing through cartomizer 100B. The tube may terminate at a mouthpiece 124 provided at or proximate to the mouthpiece-side end 108 of cartomizer 100B. Accordingly, when a user inhales through mouthpiece 124, an air flow is generated from air hole 118, through the at least one additional air holes and battery-side end air holes, and further through tube 122, terminating at mouthpiece. Upon establishing this airflow, pressure switch 114 may identify a pressure differential generated from this airflow, which may in turn activate vaporizer 100. In order to facilitate pressure switch 114 in detecting a pressure differential, pressure switch 114 may be held or encapsulated in an compressible or elastic material 126, which in one embodiment is rubber or an elastomer, thereby preventing air from flowing around pressure switch 114.

After detecting a pressure differential, pressure switch 114 may communicate with PCB 116 in order to activate vaporizer 100. As may be controlled by a program operating on PCB 116, upon detection of a pressure differential a current may be sent through the electronic circuitry to a heating element 128 provided in cartomizer 100B. Heating element 128 may be any known or to be discovered material which elevates in temperature once a current passed through the material, and in one embodiment heating element 128 may be substantially composed of nichrome wire. Heating element may be provided within proximity to a storage component 130 for a vaporizable substance, such that heating element may elevate the temperature of a vaporizable substance stored in the storage component 130 to a vaporization temperature, at which point the vaporizable substance may become a gaseous form inhalable by the user through tube 122 and mouthpiece 124. In some embodiments, storage component includes a porous material, such as fiber bating, which may be soaked with a liquid vaporizable fluid. A wick, connected with or otherwise in communication with storage component 130, may be intertwined with heating element 128 in order to facilitate delivery of vaporizable fluid to heating element 128.

PCB 116 may include a series of illuminable indicators 132, which in some embodiments may be light emitting diodes (LED). In the illustrated embodiment, a series of five (5) LED indicators 132 are provided. A series of holes in outer shell 110A may be provided so that indicators 132 are externally viewable. PCB 116 may further operate to detect voltage remaining of battery 112, such that the LED lights 132 may illuminate depending on the voltage remaining. For instance, if battery 112 operates with 4.1V or more, all five indicators 132 may illuminate, however as the voltage drops only a subset of indicators may illuminate. In some embodiments, if battery 112 has less than 4.1V, only four indicators illuminate; if less than 3.9V, only three indicators illuminate; if less than 3.7V, only two indicators illuminate; if less than 3.5V, only one indicator illuminates; and if less 3.3V, no indicators illuminate. Other predetermined voltage levels may be used depending on factors, such as battery type and power required to operate vaporizer 100. Further components of PCB 116 may include a microcontroller for executing one or more control programs, output transistor and various passive components, embodiments of which are illustrated in FIG. 4A on a side opposite of indicators 132. In addition to operating indicators 132, PCB 116 may further include a time operation, such that when vaporizer 100 has been active for longer than a pre-set time period, the PCB 116 may automatically stop the vaporizer's functioning by ceasing current to heating element 128. This cutoff time mechanism may improve the safety of vaporizer 100. The cutoff time may be, for example, ten (10) seconds of continued activation of vaporizer 100. Furthermore, PCB 116 may detect when battery portion 100a is connected to a charger (not illustrated) in order to recharge battery 112. The charger may include threading matable with the threading of the battery portion 100A provided proximate to end 104. Upon detection of a charging state, PCB 116 may operate to illuminate one or more indicators 132 in order to visually indicate to a user of vaporizer 100 that it was entered into the charging state. Once battery 112 is recharged to an optimum voltage capacity, the PCB 116 may adjust indicators 132 in order to emit an alternative visualization to the user indicating a charged state. In one embodiment, as the battery voltage capacity increase during charging, indicators 116 may be sequentially illuminated as charge returns the battery, until all indicators 116 all illuminated in order to indicate that vaporizer 100 has reached a charged state.

Vaporizer sleeve 200 may be dimensioned to conform with the dimensions of cartomizer 100B such that sleeve 200 may slide over and cover cartomizer 100B. Sleeve 200 may be slightly longer than cartomizer 100B and, as such, may be held into place by retaining ring 134 provided about battery portion 110A at or near proximate end 104. Retaining ring 134 may operate to press against the inner surface of sleeve 200, thereby holding sleeve 200 in place from frictional force. Retaining ring 134 may be embedded in a recess in outer shell 110A, thereby maintaining the position of retaining ring 134. Sleeve 200 may further include a mouthpiece hole 206 which may be aligned with mouthpiece 124 once sleeve 200 is placed over cartomizer 100B. In some embodiments, sleeve 200 and outer shell 110A may include a complimentary motif or design. Examples of such a design are illustrated in U.S. Design App. Ser. No. 29/487,413, the entire contents of which are herein incorporated by reference in their entirety.

The descriptions set forth above are meant to be illustrative and not limiting. Various modifications of the invention, in addition to those described herein, will be apparent to those skilled in the art from the foregoing description. Such modifications are also intended to fall within the scope of the concepts described herein. The disclosures of each patent, patent application and publication cited or described in this document are hereby incorporated herein by reference, in their entireties.

The foregoing description of possible implementations consistent with the present disclosure does not represent a comprehensive list of all such implementations or all variations of the implementations described. The description of some implementation should not be construed as an intent to exclude other implementations. For example, artisans will understand how to implement the invention in many other ways, using equivalents and alternatives that do not depart from the scope of the invention. Moreover, unless indicated to the contrary in the preceding description, none of the components described in the implementations are essential to the invention. It is thus intended that the embodiments disclosed in the specification be considered as illustrative, with a true scope and spirit of the invention being indicated by the following claims

What is claimed:

1. A vaporizer comprising:
   a battery portion including an outer shell having an outer shell diameter, a plurality of holes thereby permitting airflow to be established through at least a section of the battery portion, and internal components housed within the outer shell, the internal components including
      a battery,
      a printed circuit board, including a microcontroller for operating a program to control the vaporizer,
      a pressure switch operable to detect a pressure differential generated when the airflow is established,
      at least one illuminable indicator which illuminates in association with charge remaining of the battery,
         wherein the at least one illuminable indicator comprises a plurality of light emitting diodes,
         wherein the PCB operates to illuminate a predetermined number of light emitting diodes after determining the battery voltage,
         wherein the plurality of light emitting diodes includes five light emitting diodes, and
         wherein all five diodes illuminate if the battery has at least first predetermined level of volts, four diodes illuminate if the battery has at least a second predetermined level of volts, three diodes illuminate if the battery has at least a third predetermined level of volts, two diodes illuminate if a the battery has at least a fourth predetermined level of volts, one diode illuminates if the battery has at least a fifth predetermined level of volts, and no diode illuminates if the battery has less than the fifth predetermined level of volts, and
      electronic circuitry housed within the outer shell, the electronic circuitry electrically connecting the battery, the printed circuit board, the pressure switch, and the at least one illuminable indicator; and
   a cartomizer including a cartomizer outer shell having a cartomizer outer shell diameter substantially similar to the outer shell diameter, the cartomizer connectable with the battery portion, the cartomizer including internal cartomizer components housed within the outer cartomizer shell, the internal cartomizer components including
      a heating element electrically connected with the electronic circuitry of the battery portion when the cartomizer and the battery portion are connected, the heating element operable to heat to a vaporization temperature when a current is passed along the heating element,
      a storage component for holding a vaporizable fluid, and
      a tube in fluid communication between the airflow of the battery portion and a mouthpiece provided on the cartomizer outer shell.

2. The vaporizer of claim 1 further comprising a sleeve having dimensions conforming with the cartomizer, the sleeve fitable over the cartomizer.

3. The vaporizer of claim 2, wherein the sleeve includes an air hole alignable with the mouthpiece of the cartomizer when the sleeve is fitted the cartomizer.

4. The vaporizer of claim 2, wherein an outer surface of the sleeve includes a pattern or color which is the same or complimentary as a pattern or color provided on an outer surface of battery portion.

5. The vaporizer of claim 2, wherein the battery portion further comprises a retaining ring provided on external area of the outer shell of the battery portion, the retaining ring contacting an internal surface of the vaporizer sleeve when the vaporizer sleeve is placed over the cartomizer and the cartomizer is connected with battery portion.

6. The vaporizer of claim 5, wherein the retaining ring is provided in a recess of the outer shell of the battery portion.

7. The vaporizer of claim 1, wherein the pressure switch is encapsulated in an elastic material in order to prevent air flow around the pressure switch.

8. A vaporizer comprising:
   a battery portion including an outer shell having an outer shell diameter, a plurality of holes thereby permitting airflow to be established through at least a section of the battery portion, a retaining ring provided externally on an area of the outer shell, and internal components housed within the outer shell, the internal components including
      a battery,
      a printed circuit board, including a microcontroller for operating a program to control the vaporizer,
      a pressure switch operable to detect a pressure differential generated when the airflow is established,
      a plurality of light emitting diodes which illuminate in association with charge remaining of the battery,
         wherein the plurality of light emitting diodes includes five light emitting diodes, and
         wherein all five diodes illuminate if the battery has at least first predetermined level of volts, four diodes illuminate if the battery has at least a second predetermined level of volts, three diodes illuminate if the battery has at least a third predetermined level of volts, two diodes illuminate if a the battery has at least a fourth predetermined level of volts, one diode illuminates if the battery has at least a fifth predetermined level of volts, and no diode illuminates if the battery has less than the fifth predetermined level of volts, and electronic circuitry housed within the outer shell, the electronic circuitry electrically connecting the battery, the printed circuit board, the pressure switch, and the at least one illuminable indicator;

a cartomizer including a cartomizer outer shell having a cartomizer outer shell diameter substantially similar to the outer shell diameter, the cartomizer connectable with the battery portion, the cartomizer including internal cartomizer components housed within the outer cartomizer shell, the internal cartomizer components including a heating element electrically connected with the electronic circuitry of the battery portion when the cartomizer and the battery portion are connected, the heating element operable to heat to a vaporization temperature when a current is passed along the heating element, a storage component for holding a vaporizable fluid, and a tube in fluid communication between the airflow of the battery portion and a mouthpiece provided on the cartomizer outer shell; and a sleeve having dimensions conforming with the cartomizer, the sleeve fitable over the cartomizer, the sleeve including an air hole alignable with the mouthpiece of the cartomizer when the sleeve is fitted the cartomizer, the retaining ring contacting an internal surface of the vaporizer sleeve when the vaporizer sleeve is placed over the cartomizer and the cartomizer is connected with battery portion.

9. The vaporizer of claim 8, wherein the retaining ring is provided in a recess of the outer shell of the battery portion.

10. The vaporizer of claim 8, wherein the pressure switch is encapsulated in an elastic material in order to prevent air flow around the pressure switch.

* * * * *